United States Patent [19]

Dürholz et al.

[11] 3,998,893
[45] Dec. 21, 1976

[54] PROCESS FOR PREPARING DINITRONAPHTHALENES

[75] Inventors: Friedrich Dürholz, Remscheid; Josef Heinen; Adolf Hamers, both of Leverkusen, all of Germany

[73] Assignee: Bayer Aktiengesellschaft, Leverkusen, Germany

[22] Filed: Jan. 23, 1976

[21] Appl. No.: 651,993

[30] Foreign Application Priority Data

Feb. 12, 1975 Germany .......................... 2505715

[52] U.S. Cl. .............................................. 260/645
[51] Int. Cl.$^2$ ......................................... C07C 79/10
[58] Field of Search ..................................... 260/645

[56] References Cited

FOREIGN PATENTS OR APPLICATIONS 973,618  10/1964  United Kingdom ............... 260/645

OTHER PUBLICATIONS

Donaldson, The Chemistry and Technology of Naphthalene Compounds, Edward Arnold, Ltd., London, 1958, pp. 145 to 154 and 163 to 166.
Ward, J. Chem. Soc., London, 1959, pp. 487 to 493.

*Primary Examiner*—Leland A. Sebastian
*Attorney, Agent, or Firm*—Burgess, Dinklage & Sprung

[57] ABSTRACT

Dinitronaphthalenes are prepared by reacting nitronaphthalene at temperatures of from 20° to 50° C which 60 to 80% strength by weight aqueous nitric acid. The resulting dinitronaphthalene is separated off in a known manner and the residual nitric acid is enriched until a concentration of 60 to 80% by weight is reached and is then recycled to the reaction.

3 Claims, No Drawings

PROCESS FOR PREPARING DINITRONAPHTHALENES

BACKGROUND

This invention relates to a process for the preparation of dinitronaphthalenes.

Dinitronaphthalene can be prepared by nitrating naphthalene or nitronaphthalene with a mixture of nitric acid and concentrated sulphuric acid (German Pat. No. 117,368, B.I.O.S. — Bericht (B.I.O.S. Report) 986, part II, page 429 and Hodgson, Whitehurst, Soc. 1945, pages 202 to 204). The dinitronaphthalene formed by the nitration forms a viscous slurry with the concentrated sulphuric acid and the dinitronaphthalene cannot be separated from this. In order to isolate the dinitronaphthalene it is necessary to dilute the reaction mixture with water.

SUMMARY

It has now been found that if dinitronaphthalenes are prepared by reacting a nitronaphthalene at a temperature of 20° to 50° C with 60 to 80% strength by weight aqueous nitric acid, the resulting dinitronaphthalene can be separated off in a conventional manner. The residual nitric acid may then be enriched with more highly concentrated nitric acid until a concentration of 60 to 80% by weight is reached and then used in a further nitrating reaction.

The process according to the invention can be illustrated by the equation which follows:

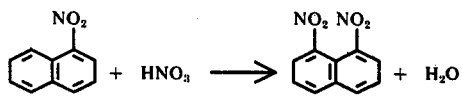

DESCRIPTION

The isomeric nitronaphthalenes, preferably 1-nitronaphthalene, can be used for the nitration according to the process of the invention.

The reaction according to the process of the invention can be carried out at temperatures from 20° to 50° C, preferably from 35° to 48° C.

In general, aqueous nitric acid is used for the nitration according to the process of the invention. The concentration of the acid employed is 60 to 80% by weight, preferably 65 to 75% by weight. In general, in the process according to the invention, 4 to 12 mols, preferably 5 to 10 mols, of nitric acid are reacted with 1 mol of nitronaphthalene.

According to the process of the invention, after the reaction the residual nitric acid is enriched with concentrated nitric acid until a concentration of 60 to 80% by weight is reached and is recycled into the reaction.

The process according to the invention can be carried out discontinuously or continuously.

For example, the process according to the invention can be carried out as follows:

The nitric acid is introduced into an open reaction vessel and the molten nitronaphthalene is added dropwise at the reaction temperature, while stirring. After the reaction has taken place, the dinitronaphthalene can be separated off with the aid of a suction filter. The nitric acid which has remained after the reaction is recycled, after enrichment, into the reaction without further purification.

The volume of highly concentrated nitric acid which is required to enrich the nitric acid which has remained after the reaction corresponds approximately to the volume of residual moisture which is separated off with the dinitronaphthalene. Thus, when the process according to the invention is carried out, the reaction volume remains virtually unchanged.

The process according to the invention has the advantage that the dinitronaphthalene can be obtained in a simple manner and in high yields. The acid which remains after the reaction can be employed again in a new reaction and does not have to be destroyed, for example by neutralisation.

Virtually only the isomeric dinitronaphthalenes are formed, in high purity, in the reaction. In the main, a mixture of isomers which consists of 1,5-dinitronaphthalene and 1,8-dinitronaphthalene is obtained.

1,5-Diaminonaphthalene and 1,8-diaminonaphthalene, which are intermediates for the preparation of the corresponding isocyanates and for the preparation of dyestuffs, are obtained from 1,5-dinitronaphthalene and 1,8-dinitronaphthalene by reduction.

EXAMPLE 1

235 g of water are introduced into a 2 l reaction beaker and 765 g of 98% strength by weight nitric acid are added, whilst stirring and cooling. In this way, 75% strength by weight nitric acid is obtained.

208 g (1.2 mols) of molten 1-nitronaphthalene are allowed to run, in the course of 1½ hours, from a dropping funnel into the nitric acid. The temperature of the reaction mixture is kept at 45° to 50° C by cooling. When the reaction is complete, the mixture is stirred further at the same temperature for about 1½ hours and cooled to about 25° C and the reaction product is separated off using a suction filter. The resulting dinitronaphthalene is washed with 2 l of water and then dried. 241 g of isomeric dinitronaphthalenes (96% of theory) having a melting point of 150° to 180° C are obtained.

EXAMPLE 2

A melt of 1-nitronaphthalene (1 mol) is pressed, in the course of 2 hours, into 75% strength by weight nitric acid (6.6 mols), whilst stirring. During the addition, the reaction mixture is kept at a temperature of 45° to 50° C by cooling.

At the start of the continuous procedure, the 75% strength nitric acid is prepared by mixing 98% strength nitric acid and water. Subsequently, the nitric acid which has remained after the reaction is employed, the losses of nitric acid being made up by adding fresh 98% strength nitric acid.

In the course of the nitration, the isomeric nitronaphthalenes crystallise out of the nitric acid and, after the mixture has been stirred for a further 2 hours, are filtered off with the aid of a suction filter. The filter cake is washed with a little 68% strength nitric acid and then with water until free from acid. After drying, a mixture of 1,5-dinitronaphthalene and 1,8-dinitronaphthalene is obtained in a yield of 85.8% of theory.

What is claimed is:

1. Process for preparing dinitronaphthalene which comprises reacting nitronaphthalene at temperatures of from 20° to 50° C with 60 to 80% strength by weight aqueous nitric acid, separating off the resulting dinitronaphthalene and enriching the residual nitric acid until a concentration of 60 to 80% by weight is reached and recycling same to the reaction.

2. Process of claim 1 wherein the reaction is carried out at a temperature of from 35° to 48° C.

3. Process of claim 1 wherein the reaction is carried out with 65 to 75% strength nitric acid.